United States Patent [19]

Wolfsen et al.

[11] 4,150,149

[45] Apr. 17, 1979

[54] METHOD AND MEANS FOR THE EARLY DETECTION AND DIAGNOSIS OF CERTAIN TYPES OF CANCERS

[75] Inventors: Ada R. Wolfsen, Fountain Valley; William D. Odell, Miraleste, both of Calif.

[73] Assignee: Professional Staff Association of the Los Angeles County Harbor General Hospital, Torrance, Calif.

[21] Appl. No.: 745,672

[22] Filed: Nov. 29, 1976

[51] Int. Cl.² .................... G01N 33/16; A61K 43/00
[52] U.S. Cl. .................................. 424/1; 23/230 B; 206/569; 424/12
[58] Field of Search ............. 23/230 B, 259 R; 424/1, 424/1.5, 12; 206/569

[56] References Cited

PUBLICATIONS

Ed. Jaffe et al., Methods of Hormone Radioimmunoassay, Academic Press, New York, 1974, pp. 125-159, 161-171, 187-195.
Gewirtz et al., Journal of Clinical Investigation, 53: 1022-1032, 1974.
Tormy et al., Cancer, 35: 1095-1100, 1975.
Baylin, Hospital Practice, Oct. 1975, pp. 117-126.
Braunstein et al., Ann. Int. Med., 78: 39, 1973.
Rees et al., Clinical Endrocrinology, 3: 263-299, 1974.
Odell et al., Ectopic Hormone, Secretion by Tumors in Cancer, ed. Becker, Plenum Press, N.Y., 1975, pp. 81 et seq.
Primack, The Production of Markers by Bronchogenic Carcinoma, A Review Seminars in Oncology, 1: 235, 1974.
Weintraub et al., Metabolism, 22: 1119, 1973.
Croll et al., ed., New Techniques in Tumor Localization and Radioimmunoassay, J. Wiley & Sons, N.Y., 1974, pp. 9-15.

*Primary Examiner*—Benjamin R. Padgett
*Assistant Examiner*—Christine M. Nucker
*Attorney, Agent, or Firm*—I. Morley Drucker

[57] ABSTRACT

This invention is directed to a method and means for the early detection of a wide variety of cancers, in humans, which method and means consists of the assay and development of a pattern or fingerprint of severally biologically inert, or inactive polypeptides (or perhaps biologically active peptides) in the blood of humans, e.g.: big-ACTH (big-Adrenocorticotropin Hormone), big-βMSH (big-beta melanocyte-stimulating Hormone), the alpha chain of the glycopeptide hormones, the measurement of the arginine vasotocin (AVT), an analogue of Arginine vasopressin, (AVP) (or the combined measurement of AVP and AVT). The values obtained by the assays of each of the foregoing polypeptids is then compared with the individual values and patterns found in humans. If any one of the polypeptide values is elevated above the upper end of the normal values, a carcinoma from some tumor site is suspected; also from the pattern of elevations in one or more peptides, a specific type of cancer may be suspected. The tumor site can then be readily localized. The level of detectability of a carcinoma from a variety of tumor sites, by means of this procedure approaches 100%. Since evidence of these biologically inactive prohormones, fragments and analogues of hormones precedes clinically recognizable ectopic hormone production by months or years, an early, reliably detection system for carcinoma cancers is set forth herein. Assays of each of the polypeptides is performed by means of radioimmunoassay coupled with radioreceptorassay or bioassay, where necessary.

23 Claims, No Drawings

METHOD AND MEANS FOR THE EARLY DETECTION AND DIAGNOSIS OF CERTAIN TYPES OF CANCERS

BACKGROUND OF THE INVENTION

The invention described herein was made in the course of work under a grant or award from the Department of Health, Education and Welfare.

Cancers frequently produce *systemic* symptoms by means of production of a variety of humoral or hormonal substances. More specifically, it has been recognized that clinically apparent ectopic hormone syndromes are manifested by *poly-peptide* hormone production. The clinically apparent ectopic polypeptide hormone syndromes that are known to be associated with nonendocrine neoplasms are listed below in the order, approximately, of the numbers of patients reported with these syndromes:

1. ACTH (ACTH=Adrenocorticotropic Hormone)
2. Alpha and beta MSH (MSH=melanocyte-stimulating hormone)
3. Gonadotropin
4. Vasopressin
5. Parathormone
6. Hypoglycemic-producing factor
7. Erythroprotein
8. Gastrin
9. Thyroid-stimulating factor
10. Hypophosphatemia-producing factor
11. Corticotropin-releasing hormone
12. Prolactin
13. Growth hormone
14. Kinins
15. Prostaglandins
16. Secretin
17. Glucagon
18. Calcitonin Following this approach, single ectopic peptide tumor markers have been described in the prior art that are useful to detect a *particular* type of cancer in a certain percentage of patients. For example, alpha fetal protein is a tumor marker for liver cancer. A tumor marker, for bronchogenic carcinoma, is Adrenocorticotropic Hormone (ACTH) and this marker is found in about 80% of patients with this type of carcinoma. Also, melanocyte-stimulating hormone (MSH) is considered to be produced in some patients with bronchogenic carcinoma.

While the foregoing approaches are useful in determining whether a *particular* type of carcinoma is present, they do not offer a solution to the development of an *early* carcinoma screening test for the wide variety of carcinoma tumor and histological types present in humans.

Much discussion in the literature centers about attempts to develop an ideal screening test which would allow early detection of cancers of a number of different tumor and histological types and would be of high specificity and high sensitivity. Ideally, of course, such a screening test should have no false negatives and no false positives.

To the best of our knowledge, no such screening test has been developed which meets these criteria even though the tremendous need for such screening procedures, along with the extremely large amount of work by many investigators, is clear. Pertinent background material of which we are aware is listed below:

Gewirtz, G. and Yalow, R. S., Ectopic ACTH Production in Carcinoma of the Lung, J. Clin., Invest. 53: 1022–1032, 1974.

Ayuazian, L. F., Schneider, B., Gewirtz, G., Yalow, R. S., Ectopic Production of big ACTH in Carcinoma of the Lung, Am. Rev. Resp. Diseases. 111:279, 1975.

Baylin, S. B., Ectopic Production of Hormones and Other Proteins by Tumors, Hospital Practice, Oct. 1975, p. 117–126.

Rees & Ratcliffe, Ectopic Hormone Production by Non-Endocrine Tumors, Clinical Endocrinology, 3:263–299, 1974.

Tormey, D. C., Wallkes, T. P., et al. Biological Markers in Breast Carcinoma Cancer 35:1095–1100, 1975.

Braunstein, G. D., J. L. Vaitukaitis, P. P. Carbone and G. T. Ross. Ectopic Production of Human Chorionic Gonadotrophin by Neoplasms, Ann Int. Med. 78:39, 1973

Odell, W. D. and A. Wolfsen, Ectopic Hormone, Secretion by Tumors in Cancer, Edited by F. B. Becker, Plenum Press, N. Y. Dec. 1975, pp 81 et seq.

Primack, A., The Production of Markers by Bronchogenic Carcinoma, A Review Seminars in Oncology 1:235, 1974.

Pritchard, V. A. V., Sutherland, W. H., Deeley, T. V., Cancer Detection, Lancet, 637, March 1976

Weintraub, B. D., and Rosen, S. W., Competitive Radioassays and Specific Tumor Markers, Metabolism 22:1119, 1973.

This invention is directed towards a method and means for achieving close to the ideal result, i.e., an early cancer screening test for carcinomas of a wide number of different tumor and histologic types, which screening procedure has a very low false positive factor and a very low false negative factor.

SUMMARY OF THE INVENTION

The advance in the art, upon which this invention is based, is predicated upon the hypothesis that elaboration of many types of *biologically inactive* polypeptides may well be a universal concomitant of neoplasia. It is believed, in fact, that the *clinically recognized* ectopic hormonal syndromes, above-mentioned, represent only a *small fraction* of the synthesizing activity of the neoplasm, and that the neoplasm, is in large measure, synthesizing biologically inactive, (including in some cases, only weakly biologically active)peptides. Further, the elaboration of such biologically inactive polypeptides by nonendocrine neoplasms may precede any other evidence of the neoplasm by months or years. While the biologically inactive polypeptides would not be found by bioassays or receptor assays, it was hypothesized, further, that such polypeptides may well be immunoreactive and thus measurable by radioimmunoassay (RIA) techniques.

Thus, if a sufficient number of the "correct" biologically inert or inactive ectopic polypeptides, produced by widely differing tumor and histological types, were identified and measurable at very low levels in blood serum of a human (or animal), a generalized diagnosis of a carcinoma, based on such early detection, might well render the neoplasm site easily locatable and thus resectable or treatable.

This invention is based on the discovery that certain "key", biologically inert or inactive, polypeptides are indeed produced, in increased levels in the blood, when carcinomas of widely varying tumor and histological types are present in a human patient.

Thus, we believed that the four most prevalent found clinically apparent ectopic hormone syndromes, ACTH, alpha and beta MSH, Gonadatropin and Vasopressin in fact, represented only a small fraction of the synthesizing activity of the neoplasm and that the neoplasm is producing in large measure, biologically inactive prohormones, biologically inactive fragments of a polypeptide, and perhaps, biologically inactive analogues of certain hormones, and other molecular components, which are only generally related to the just-mentioned four clinically apparent ectopic hormone syndromes. In fact, we have substantiated within 95% confidence limits, that what we postulated does, in fact, occur. This has lead to the basis of this invention: a carcinoma screening procedure that requires the assay of only the following biologically inert, or inactive polypeptides:

1. big-ACTH (that ACTH which is larger than 1–39 aminoacid ACTH);
2. big-βMSH;
3. α chain of the glycopeptide hormone; and
4. AVT; (or AVT+AVP). (AVT=Argenine vasotocin, and is an analogue of Argenine vasopressin (AVP).

big-ACTH and bigβMSH are biologically inert prohormones. The α chain of the glycopeptide hormone is also biologically inert. AVT is weakly biologically active to an extent insufficient to cause any clinically recognizable syndrome.

The levels of each of the four polypeptides are measured in the blood of each patient to be screened, and then compared with the upper end of the normal levels, i.e., those levels found in noncancerous patients. If the level of *any one* of the four polypeptides lies above the upper end of the normal level, a carcinoma derived from any one of a variety of different tumor types must be suspected.

Once elevation of one of the polypeptides is found, localization of the neoplasm site is accomplished by assaying blood samples for the elevated peptide marker, or markers, taken from venous drainage of each possible tumor site.

Sensitive radioimmunoassay (RIA) methods for detecting very low levels of biologically inactive total ACTH are performed, followed by a radioreceptorassay, or other bioassay, to determine small-ACTH (1–39 amino acid ACTH). By this double assay technique, big ACTH is precisely measured in the blood of the patient. RIA methods are also preferably employed to measure the level of big-βMSH and the α chain of the glycopeptides. An RIA method for simultaneous measurement of AVP and AVT is presently employed-which can be then combined with an RIA or other assay for AVP, to determine AVT by difference, if desired.

The RIA and RRA techniques, utilized by us, and to be described herein, in detail, enables cancer screening tests to be performed, for a wide variety of tumor and histological types within a percentage of detectability approaching 100%–based on a study of 157 patients.

With such a reliability factor, early detection of carcinomas of a number of different tumor and histological types is possible. The tumor types for which it is presently believed that our cancer screening procedure is applicable are those of: liver, lung, pancreas, thymus, esophagus, colon, breast, stomach, bladder, bile duct, and kidney. These tumors may be of various histological types including squamous-cell carcinoma, adeocarcinoma and Oat-cell carcinoma.

The foregoing list of tumor and histological types is not believed to be a complete list of the tumors and histological types to which our screening test is applicable. As research progresses, it is believed that the list of tumor and histological types will be considerably expanded, e.g., to non-carcinoma cancers.

The screening procedure of this invention was utilized with 157 patients having carcinomas of the lung and colon. Elevated levels of at least one of big-ACTH, big-βMSH, α chain of the glycopeptide hormone, and AVT (or AVT+AVP) were found in the blood of 95% of these patients. The screening system of this invention was also utilized with 28 patients having carcinomas of the liver, pancreas, thymus, esophagus, breast, stomach, bladder, bile duct, and kidney. In these cases, assay of tissue extracts of the tumors of every one of the patients showed elevated levels of at least one of the foregoing polypeptides. It is expected that those polypeptides elevated in the tissue of the tumor will be secreted into the blood, and will then be found in elevated levels, as with the carcinomas of the lung and colon.

This cancer screening procedure can be readily employed by hospitals, clinics, and laboratories having RIA apparatus utilizing a kit, or group of reagents, which includes, for each of the polypeptide markers to be assayed:

(a) Known quantity of radioactive peptide of the type to be assayed;
(b) Known quantity of peptide of the type to be assayed for preparation of standard curves; and
(c) An antibody or tissue receptor specific for the binding of the peptide of the type to be measured.

DESCRIPTION OF THE PREFERRED EMBODIMENT

A. COLLECTION OF BLOOD SAMPLES

Blood samples are drawn from the patient into lightly heparinized tubes and immediately, i.e., at the bedside, placed on ice. These samples are then transported to a refrigerated centrifuge and rapidly centrifuged. The plasma is aspirated and immediately frozen at −70° C. This procedure is believed to be necessary because the polypeptides to be assayed are extremely labile.

The blood samples, for each patient, then proceeds through a series of sensitive RIA procedures (and one RRA procedure) for the peptide markers, each of which procedures will be detailed hereinafter. The elevation of any of the polypeptides markers above that of the upper end of the normal range, will be cause for concern that a carcinoma is present. This knowledge then permits localization of the tumor source, as earlier described.

With this general procedural outline, the methodology for assaying each of the polypeptide marks will be set forth.

B. big-ACTH MEASUREMENT big forms of ACTH (i.e., forms of ACTH larger and more acidic than the 1–39 amino acid ACTH) have been described (Gewirtz and Yalow, 1973). It appears clear that, in some instances, the big-ACTH is elaborated in a larger quantity by neoplasms than in a conventional hypersecretory endocrine state. We have assayed big-ACTH in both plasma and tissue extracts by means of a novel double assay system.

First, a very sensitive (4 picogram/ml. plasma) RRA[1] is utilized which quantifies biologically active little-ACTH (i.e., the 1-39 amino acid ACTH) and shows little, if any, reaction with biologically inactive big-ACTH. RRA procedures are based on the same principles as RIA procedures but utilize a target tissue hormone receptor as the assay binding protein, instead of an antibody. In the Wolfsen et. al method, for RRA of ACTH (footnote 1) the adrenal cortex membrane receptor is employed as the binding protein.

[1] (Wolfsen, A., McIntyre, H. B. and Odell, W. D. Adrenocorticotropin measurement by competitive binding receptor assay. J. Clin Endo and Metab. 34:684, 1972).

A highly sensitive standardized RIA technique is next performed for ACTH (Berson & Yalow, JCI 47:2725) which RIA measures both big and little ACTH. Thus, highly precise big-ACTH is measured which can be compared to normal values.

An an illustration of the magnitude of the elevation of big-ACTH, as compared to "normal" values, blood plasma samples were taken from human patients with untreated, and treated, cancer of the lung, and from patients with cancer of the colon. Blood samples were also taken from human patients with chronic obstructive pulmonary Disease (COPD). The values of big-ACTH, as determined by the double assay technique above-described, were then compared with normal values obtained from a population of 38 non-cancer human subjects.

The results are set forth in TABLE I.

TABLE I

| CLINICAL STATE OR DISEASE | big-ACTH mean ± sem pg/ml* | N** |
|---|---|---|
| Normal | 56.5 ± 4.2 | 38 |
| Cancer lung (untreated) | 232 ± 38 | 57 |
| Cancer lung (treated) | 105 ± 17.4 | 60 |
| Cancer Colon (treated) | 265 ± 4.2 | 73 |
| COPD | 82.6 ± 8.5 | 45 |

*pg/ml = picogram per milliliter blood serum.
**N = number of human patients.

In further confirmation of the production of elevated big-ACTH by such nonendocrine neoplasms, frozen sections of tissue extracts of patients with carcinoma of the lung were prepared and assayed for big-ACTH. All such tumors, whether treated or untreated, showed concentrations of big-ACTH greater than 1,000 pg/gm tissue extract.

TABLE II shows the percentages of patients with carcinomas of lung and colon who had elevated levels of big-ACTH. (The upper limits of the normal value, within 95% Confidence Limits, of big-ACTH was found to be 100 pg/ml. plasma. All values found in human patients above 100 pg/ml plasma were therefore defined as "elevated" levels for the purpose of TABLE II, and for our screening procedure in general).

TABLE II

| CLINICAL STATE OR DISEASE | PERCENTAGE OF PATIENTS WITH ELEVATED bit-ACTH | | |
|---|---|---|---|
| Carcinoma lung | 17/25* | (68%) | in blood |
| Carcinoma colon | 26/30+ | (87%) | in blood |
| Normal lung | 0/5 | (0%) | in tissue extract |
| Normal colon | 0/5 | (0%) | in tissue extract |

*19 patients - 25 samples
+17 patients - 30 samples

In this study, the production of elevated levels of big-ACTH in these non-endocrine neoplasms was further confirmed by the assay of the tissue extracts of carcinoma of the lung and colon. Elevated levels of big-ACTH were found in 100% of such extracts. That the ACTH in the tissue extracts was big-ACTH was confirmed using Sephadex chromatophotography (G-50).

Using RRA techniques, ACTH (i.e., little ACTH) was not elevated in those same samples from cancer patients who did not have the clinically recognizable ectopic ACTH syndrome (17 patients). Only in the presence of the clinically recognizable syndrome, was blood ACTH elevated by RRA as well as by RIA. This confirms the importance of the assay of big-ACTH as a tumor marker, as opposed to the assay of little-ACTH.

TABLE III lists the data obtained from patients who were studied, on a blind basis, for evaluation of an abnormal small mass, or other abnormality, found in a chest X-Ray. Results were matched after a pathological diagnosis had been obtained.

TABLE III

| Clinical Condition | big-ACTHJ mean ± sem (pg/ml) | N |
|---|---|---|
| Benign lesion | 56.7 ± 4.9 | 22 |
| Carcinoma lung | 232 ± 38 | 54 |

In this study, 75% of the patients with untreated lung carcinoma had significantly elevated big-ACTH concentrations. 22% (10 patients) with severe obstructive pulmonary disease showed elevated big-ACTH concentrations, and of these 10 patients, three were subsequently shown to have carcinoma of the lung.

C. big BETA-MELANOCYTE STIMULATING HORMONE (big-βMSH)

βMSH immunoactivity has been quantified by a recently described RIA[2] which has a sensitivity of 7 pg/ml plasma. This RIA requires conjugation of synthetic 1-22 h βMSH to bovine thyroglobulin, and immunization of rabbits. A sufficiently high affinity antisera (it was also high titer) was obtained to permit quantification of MSH in levels considered to be circulating in normal humans. However, in studies of non-cancer patients, it appears that βMSH per se does not circulate in blood of humans—the so-called "βMSH" immunoreactivity is due to a larger molecular weight peptide—probably β lipotropin. The peptide, β lipotropin, includes the βMSH fragment, and thus the true immunoreactivity that we measure, and which we have found to be the significant tumor marker is the β lipotropin hereinafter, and in the claims, termed big-βMSH or big-hβ-MSH.

[2] Bachelot, 1, A. Wolfsen and W. O. Odell, βMSH—an artifact of protein purification, Clin. Research 24:130A, 1976, full paper submitted to J. Clin. Endocrinol. Metab. in press.

An an illustration of the magnitude of elevation of big-βMSH, as compared to normal values, blood plasma samples were taken from human patients with untreated, and treated, lung carcinoma, as well as from patients with carcinoma of the colon. Blood samples were also taken from human patients with COPD. The values of big-βMSH were determined, by the method of Bachelot et al, supra, for both cancer patients and normal patients. The results are set forth in TABLE IV.

TABLE IV

| CLINICAL STATE OR DISEASE | big-βMSH mean ± sem (pg/ml.) | | | N |
|---|---|---|---|---|
| NORMAL | 27.4 | ± | 2.0 | 44 |
| Carcinoma Lung (untreated) | 108 | ± | 14.7 | 57 |
| Carcinoma Lung (treated) | 49.9 | ± | 10.9 | 58 |
| Carcinoma Colon (treated) | 31.6 | ± | 3.8 | 76 |
| COPD | 38.6 | ± | 7.4 | 70 |
| Cirrhossis | 23.8 | ± | 2.6 | 20 |
| Inflammation of the Bowel | 29.5 | ± | 4.0 | 14 |

TABLE V shows the elevation of big-βMSH in terms of percentages of patients with carcinomas of lung, colon and kidney. (The upper limits of the Normal value, within 95% Confidence Limits, of big-βMSH was found to be 52 pg/ml plasma. All values of big-βMSH found in human patients, above 52 pg/ml plasma, were therefore defined as "elevated" levels for the purposes of TABLE V, and for our screening procedure, in general).

TABLE V

| CLINICAL STATE OR DISEASE | PERCENTAGE OF PATIENTS WITH ELEVATED big-βMSH |
|---|---|
| Carcinoma lung | 24/34* (71%) in blood |
| Carcinoma colon | 6/30+ (20%) in blood |
| Carcinoma kidney | 4/5 (80%) in blood |

In this study, the production of elevated levels of big-βMSH, in the colon and lung non-endocrine neoplasms, was further confirmed by assay of the tissue extract of the lung and colon carcinomas. Elevated levels of big-βMSH, in excess of 1,000 pg/gm tissue, was found in 27/28 (97%) lung carcinoma patients, and in 18/18 (100%) colon carcinoma patients.

TABLE VI lists data obtained from patients who were studied, on a blind basis, for evaluation of an abnormal small mass or "coin lesion", or other abnormality found as a result of a chest X-Ray. Results were matched after a pathological diagnosis had been obtained.

TABLE VI

| CLINICAL STATE OR DISEASE | big-βMSH mean ± sem (pg/ml) | | | N |
|---|---|---|---|---|
| Benign lesion | 30.0 | ± | 2.3 | 33 |
| Carcinoma lung | 101 | ± | 13.6 | 52 |

*32 patients - 34 samples
+26 patients - 30 samples

In this study, 63% of patients with untreated localized lung carcinoma had significantly elevated big-βMSH blood concentration. 14% of the patients with severe obstructure pulmonary disease showed elevated big-βMSH levels, and one of these patients, with elevated big-βMSH was subsequently shown to have carcinoma of the lung.

D. ALPHA CHAIN OF THE GLYCOPEPTIDE HORMONE

The glycopeptide hormones, (thyroid—stimulating hormone, luteinizing—stimulating hormone, follicle stimulating hromone, and human chorionic gonadotropin, TSH, LH, FSH, and hCG, respectively) have immunological and hence structural similarities. The alpha peptide chains of TSH, LH and FSH have identical amino acid sequences; the alpha chain of hCG is nearly identical to the alpha chain of TSH, LH and FSH.

It is recognized that the blood of hypothyroid patients and postmenopausal women have circulating alpha chain, and that free alpha chains are secreted by the normal pituitary.[3,4] It was also found, however, that free alpha chains are elaborated by a variety of neoplasms in amounts that are, in most instances, significantly higher than the normal values found in man and women. Our results are set forth below in TABLE VII:

TABLE VII

| CLINICAL STATE OR DISEASE | αCHAIN OF THE GLYCOPEPTIDE HORMONE - log mean ± sem (μU/ml) | | | |
|---|---|---|---|---|
| | MALES | N | FEMALES | N |
| NORMAL | 19.1 ± 1.5 | 13 | 37.1 ± 5.9 | 12 |
| Lung Carcinoma (untreated) | 51.6 ± 8.7 | 42 | 36.5 ± 5.2 | 12 |
| Colon Carcinoma (treated) | 43.1 ± 11.1 | 22 | 73.6 ± 9.1 | 24 |

[3]Edmonds, M., M. Molitch, J. Pierce and W. D. Odell. Secretion of alpha and beta subunits of TSH by the anterior pituitary. Clin Endo 4:525, 1975.
[4]Edmonds, M., M. Molitch, J. Pierce and W. D. Odell. Secretion of apha subunits of luteinizing hormone by the anterior pituitary. J Clin Endo & Metab. 41:55, 1975.

The percentage of cancer patients having elevated α chain of the glycopeptide hormone is set forth in TABLE VIII. (The upper limits of the Normal value, within 95% Confidence limits, of the α chain of the glycopeptide hormone is as follows:

Males—37 ul/ml plasma
Females—premenopausal—42 ul/ml plasma
Females—postmenopausal—102 ul/ml plasma All values of the α chain found, in human patients, above these levels were therefore defined as "elevated" levels for the purposes of TABLE VII, and for our screening procedure, in general).

TABLE VIII

| CLINICAL STATE OR DISEASE | % OF PATIENTS WITH ELEVATED αCHAIN OF THE GLYCOPEPTIDE HORMONE | |
|---|---|---|
| | MALES | FEMALES (Over Age 50) |
| Lung Carcinoma blood | 15/40 (30%) | 2/7 (29%) |
| Colon Carcinoma blood | 11/42 (20%) | 12/36 (31%) |
| Misc. Other Carcinomas - blood | 9/10 (89%) | — |

The alpha chain of the glycopeptide hormone is therefore found to be a useful tumor marker.

The alpha chain of the glycopeptide hormone was quantified by the RIA procedure described in Binoux, Pierce and Odell, J. Clin. Endocrinol and Metab., 38:674, incorporated herein by this reference.

E. ARGININE VASOPRESSIN (AVP) AND ARGININE VASOTOCIN (AVT)

It has also been found that AVP and AVT, taken as one entity, is an important tumor marker in the screening procedure.

By way of background, vasopressin is an eight amino acid* peptide predominantly elaborated in ectopic syndromes by carcinomas of the lung. When this biologically active peptide is produced, a syndrome of hyponatremia, persistently hyperosmotic urine, and difficulty with sodium conversion is produced. This peptide has been identified by bioassay and also known to be structurally similar or identical to arginine vasopressin by radioimmunoassays. Bartter and Schwartz (1967) and Vorherr et al. (1968) reported a large series of patients in whom the tumor vasopressin reacted identically to arginine vasopressin in radioimmunoassays. It is not known whether neoplasms commonly elaborate octapeptides other than arginine vasopressin, but Viszolyi and Perks (1969) have shown by bioassays and Skowsky and Fisher (1973) by radioimmunoassay that the fetal pituitary does elaborate arginine vasotocin (AVT). AVT is biologically inactive in the sense that it does not produce a clinically recognizable syndrome—probably because it is secreted at such low levels into the blood.

*The two half-cysteine residues are considered as one amino acid (cystine).

A normal range of AVP and AVT activity has been established, and blood samples of patients are assayed for AVP and AVT by RIA techniques. Elevated AVP plus AVT readings are found to be a significant tumor marker. The upper limits of the Normal value, within 95% Confidence limits, of AVP+AVT was found to be 3 $\mu$U/ml. plasma. All values of AVP±AVT, in human patients, above this value were therefore defined as "elevated" levels for the purpose of our screening procedure. We have found that 40% of patients with lung carcinoma (41 patients) had elevated levels of AVP+AVT, and 40% of patients with colon carcinoma (23 patients) had elevated levels of AVP+AVT.

AVP and AVT activity may be simultaneously quantified by a sensitive RIA assay, such as that described in Rosenbloom and Fisher, 1975, Endocrinology 95:1726, 1974, and incorporated herein by this reference. In this method, the simultaneous assay of blood samples containing both AVP and AVT is conducted with an antisera which measures both AVP and AVT. Also, RIA for AVP alone may be performed, e.g., by the RIA method of Skowsky, Rosenbloom and Fisher, J. Clin. Endocrinol. Metab. 38:278, 1974, which method is incorporated herein by this reference. The AVT values are determined by the difference between the AVP+AVT value, and the AVP value alone. The usefulness of the AVP+AVT assay can be further seen from the data in TABLE IX.

TABLE IX

| CLINICAL CONDITIONS OR DISEASE | AVP + AVT Mean ± Sem ($\mu$U/ml) | N |
|---|---|---|
| Normal - Blood | 1.2 ± 0.1 | 46 |
| Carcinoma lung (untreated) blood | 3.3 ± 0.4 | 41 |
| Carcinoma colon - blood | 2.3 ± 0.4 | 23 |

In summary, the assay of the combination of: the two biologically inert prohormone markers, big-ACTH and big-$\beta$MSH, the biologically inert peptide fragment, the $\alpha$ chain of the glycopeptide hormone, and the assay of the marker unit of AVP and AVT (or AVT alone) followed by a comparison of the assay values with normal values to detect elevation of any one of the peptides offers a means of early detection of carcinomas of a wide variety of types of tumors and histological types, the level of detectability approaching 100%.

As previously mentioned, we tested eighty (80) patients with either lung or colon carcinoma and found elevated levels, in blood, of at least one of big-ACTH, big-$\beta$MSH, $\alpha$chain of the glycopeptide hormone, and AVT (or AVT+AVP). Because of our similar findings, in tissue extracts, of carcinomas of a variety of other tumor sites, as previously mentioned, it is expected that the screening procedure of this invention will be of use in detecting carcinomas of a wide variety of tumor types and histological types.

Other biologically inert or inactive polypeptide markers, may appear at a later time, and be utilized as part of the assay procedure in order to render it of even wider scope and of even greater reliability.

F. THE REAGENT KIT

The kit, or groups of reagents, preferably utilized in our screening procedure are designed for use with RIA apparatus and procedures. The kit preferably includes the following reagents:

1. Reagents for quantifying big-ACTH:
   (a) a known quantity of radioactive ACTH,
   (b) a known quantity of anitbody specific for the binding of ACTH;
   (c) a known quantity ACTH for preparation of standard curves;
   (d) a known quantity of reagent for separating antibody bound radioactive ACTH from free radioactive ACTH for measurement of the level of ACTH in said human serum, and
   (e) means such as the reagents of the RRA procedure of Wolfsen et al., supra for measuring the level of 1–39 amino acid ACTH whereby the big-ACTH level is calculated.

2. Reagents for quantifying big-h $\beta$MSH preferably include:
   (a) a known quantity of radioactive big-h $\beta$MSH, or small-h $\beta$MSH (which binds equally well to the antibody),
   (b) a known quantity of antibody specific for the binding of the big or small-h $\beta$MSH;
   (c) a known quantity of big-h $\beta$MSH for preparation of standard curves, and
   (d) a known quantity of reagent for separating antibody bound radioactive big-h $\beta$MSH from free radioactive big-h $\beta$MSH for measurement of big-h $\beta$MSH in humans.

3. Reagents for quantifying the $\alpha$ chain of the glycopeptide hormone preferably include:
   (a) a known quantity of radioactive $\alpha$ chain of the glycopeptide hormone,
   (b) a known quantity of antibody specific for the binding of said $\alpha$ chain of the glycopeptide hormone,
   (c) a known quantity of said $\alpha$ chain of the glycopeptide hormone for preparation of standard curves, and
   (d) a known quantity of reagent for separating antibody bound radioactive $\alpha$ chain of the glycopeptide hormone from free radioactive α chain of the glycopeptide hormone.

4. The reagents for quantifying the level of AVP plus AVT, preferably include:
 (a) a known quantity of radioactive AVP,
 (b) a known quantity of antibody specific for the binding of both AVP and AVT,
 (c) a known quantity of AVP and AVT for preparation of standard curves, and
 (d) a known quantity of reagent for separating antibody bound radioactive AVP and AVT from free radioactive AVP and AVT for measurement of the level of AVP plus AVT in human serum.

5. The reagents for quantifying the level of AVP may also be included, as set forth in the RIA procedure of Skowsky, Rosenbloom and Fisher, supra, in order to determine the AVT value by difference.

6. Reagents are to be included for buffering the human serum to varying pHs for the various assays to be performed, if desired. The term "human serum" as used herein, and in the claims, encompasses human serum or plasma which has been subjected to further extraction procedures, e.g., procedures to concentrate ACTH, and AVP+AVT prior to the assay for the peptides involved; the term also encompasses an unextracted human serum, i.e., one in which no further extraction procedure is necessary, as when assaying for big-h βMSH and the α chain of the glycopeptide hormones by the RIA methods herein incorporated by reference.

G. THE RIA METHODS

The reagent kits above-described are used in RIA procedures to which specific references have been made heretofore. The RIA procedures generally include, for each of the peptides, the following steps:

1. adding, to a measured quantity of human serum,
 (a) buffering ions to buffer said serum;
 (b) radioactive peptide, of the type to be measured, in an amount which will give a measurable counting rate of either antibody bound or free radioactivity after reaction equilibrium has been reached as set forth in Step 2 below; and
 (c) an antibody in sufficient quantity to bind a significant quantity of the radioactive peptide in the absence of any of the non-radioactive peptide to be measured;
2. allowing reaction of both the particular peptide and said radioactive peptide with said antibody to proceed substantially to equilibrium to thereby produce an antibody bound radioactive peptide;
3. separating said antibody bound radioactive peptide to be measured from said free radioactive peptide;
4. measuring the quantity of radioactive peptide selected from antibody bound radioactive peptide and free radioactive peptide;
5. preparing a standard curve with known amounts of the particular peptide to be measured; and
6. correlating the quantity of radioactive peptide measured with a known amount of said peptide read from said standard curve.

For the big-ACTH measurement, the double assay approach is required wherein we quantify total ACTH by the RIA procedure above generally outlined, followed by quantifying the 1-39 amino acid ACTH—preferably by tissue receptor assay. The double assay approach is employed also, if it is desired to measure AVT values, as opposed to AVP and AVT values, by following the above-generally outlined RIA for AVP+AVT values, by performing an RIA for AVP, and ascertaining AVT, by difference.

The method and means of accomplishing the objectives of this invention may be modified by those skilled in the art. Hence, we do not intend to be limited by the specific examples and illustrations set forth herein, but only by the claims which follow.

We claim:

1. A kit for the screening of cancer of certain tumors and histological types in humans, which includes the combination of:
 (i) means, for quantifying the level of a peptide selected from the group consisting of big-ACTH (big-Adrenocorticotropen Hormone), ACTH, and 1-39 amino acid ACTH in human serum;
 (ii) means, for quantifying the level of big-βMSH (big-βmelanocyte-stimulating hormone) peptide in human serum;
 (iii) means, for quantifying the level of the alpha chain of glycopeptide hormone in human serum; and
 (iv) means, for quantifying the level of the peptide selected from the group consisting of Argenine vasotocin (AVT) and Argenine vasopressin (AVP) plus Argenine vasotocin (AVT) in human serum, each of said means for each of said peptides including in containers a known quantity of radioactive peptide of each type to be assayed, a binding agent specific for the binding of the peptide of the type to be assayed, and a known quantity of the peptide to be assayed for preparation of a standard curve.

2. The kit of claim 1, which further includes containers of buffer for the buffering of human serum.

3. The kit of claim 1 in which the means for quantifying big-ACTH further includes in containers:
 a known quantity of reagent for separating antibody bound radioactive ACTH from free radioactive ACTH for measurement of the level of ACTH in said human serum.

4. The kit of claim 3 which further includes containers of buffer for the buffering of human serum.

5. The kit of claim 1, in which the means for quantifying big-ACTH further includes in containers:
 a known quantity of reagent for separating antibody bound radioactive ACTH from free radioactive ACTH for measurement of the level of ACTH in said human serum;
 a known quantity of tissue receptor specific for the binding of 1-39 amino acid ACTH; and
 a known quantity of reagent for separating antibody bound radioactive 1-39 amino acid ACTH from free radioactive 1-39 amino acid ACTH for measurement of 1-39 amino acid ACTH.

6. The kit of claim 5 which further includes containers of buffer for the buffering of human serum.

7. The kit of claim 1 which further includes in containers:
 a known quantity of reagent for separating antibody bound radioactive hβMSH from free radioactive hβMSH for measurement of big-hβMSH in humans.

8. The kit of claim 7 which further includes:
 containers of buffer for the buffering of human serum.

9. The kit of claim 1 which further includes in containers:

a known quantity of reagent for separating antibody bound radioactive α chain of the glycopeptide hormone from free radioactive α chain of the glycopeptide hormone.

10. The kit of claim 9 which further includes containers of buffer for the buffering of human serum.

11. The kit of claim 1, in which the means for quantifying the level of AVP plus AVT, includes in containers:
a known quantity of radioactive Argenine vasopressin (AVP);
a known quantity of antibody specific for the binding of both AVP and AVT;
a known quantity of AVP and AVT for preparation of standard curves; and
a known quantity of reagent for separating antibody bound radioactive AVP and AVT from free radioactive AVP and AVT for measurement of the level of AVP and AVT in human serum.

12. The kit of claim 11, which further includes:
means for quantifying the level of AVT plus AVP; and
means for quantifying the level of AVP, to thereby enable quantification of AVT by difference.

13. The kit of claim 1 in which the means for quantifying big-ACTH includes in containers:
a known quantity of reagent for separating antibody bound radioactive ACTH from free radioactive ACTH for measurement of the level of ACTH in said human serum; and
means for measuring the level of 1-39 amino acid ACTH whereby the big-ACTH level is calculated;
the means for quantifying big-h βMSH includes in containers:
a known quantity of reagent for separating antibody bound radioactive h βMSH from free radioactive h βMSH for measurement of big-h βMSH in humans;
the means for quantifying the α chain of the glycopeptide hormone includes in containers:
a known quantity of reagent for separating antibody bound radioactive α chain of the glycopeptide hormone from free radioactive α chain of the glycopeptide hormone; and
the means for quantifying the level of AVP plus AVT, includes in containers:
a known quantity of reagent for separating antibody bound radioactive AVP and AVT from free radioactive AVP and AVT for measurement of the level of AVP and AVT in human serum.

14. The kit of claim 13 which further includes containers of buffer for the buffering of human serum.

15. The kit of claim 13 which includes in addition:
means for quantifying the level of AVP to thereby enable quantification of AVT by difference.

16. A method of screening for carcinoma of certain tumor and histological types in humans, which includes the combination of the following steps:
(i) measuring the level of big-ACTH (big-Adrenocorticotropin Hormone) peptide in human serum by radioimmunoassay of ACTH, assay of 1-39 amino acid ACTH, and calculating the difference as big-ACTH;
(ii) measuring the level of big-βMSH (big-βmelanocyte-stimulating hormone) peptide in human serum by radioimmunoassay;

(iii) measuring the level of the α chain of glycopeptide hormone in human serum by radioimmunoassay;
(iv) measuring the level of the peptide selected from the group consisting of argenine vasotocin (AVT) and argenine vasopressin (AVP) plus argenine vasotocin (AVT) in human serum by radioimmunoassay the steps (i) through (iv) being performable in any sequence;
each radioimmunoassay including a measurement of the free or bound radioactive peptide; and
comparing the level of each of said peptides with normal values circulating in the blood of humans to determine the elevation, if any, of any of said peptides.

17. The method of claim 16 in which the assay of 1-39 amino acid ACTH is performed by a tissue receptor assay.

18. The method of claim 16 which includes quantifying the level of big-Adrenocorticotropin Hormone (big-ACTH) by:
A. adding, to a measured quantity of human serum,
 (a) buffering ions to buffer said serum;
 (b) radioactive ACTH, in an amount which will give a measurable counting rate of either antibody bound or free radioactivity after reaction equilibrium has been reached as set forth in Step B below; and
 (c) an antibody in sufficient quantity to bind a significant quantity of said radioactive ACTH in the absence of any of the nonradioactive ACTH to be measured;
B. allowing reaction of both ACTH, to be measured, and said radioactive ACTH, with said antibody to proceed substantially to equilibrium to thereby produce an antibody bound radioactive ACTH;
C. separating said antibody bound radioactive ACTH, to be measured, from said free radioactive ACTH;
D. measuring the quantity of radioactive ACTH selected from antibody bound radioactive ACTH and free radioactive ACTH;
E. preparing a standard curve with known amounts of the ACTH to be measured;
F. correlating the quantity of radioactive ACTH measured with a known amount of said ACTH read from said standard curve;
G. quantifying the level of 1-39 amino acid ACTH; and
H. determining the quantity of big ACTH by substracting the measured quantity of 1-39 amino acid ACTH from the quantity of ACTH determined by the procedure of Steps A-F.

19. The method of claim 10 which includes quantifying the level of big-βmelanocyte-stimulating hormone (big-h βMSH) by:
A: adding, to a measured quantity of human serum,
 (a) buffering ions to buffer said serum;
 (b) radioactive h βMSH peptide selected from the group of big-h βMSH and small-h βMSH peptide, in an amount which will give a measurable counting rate of either antibody bound or free radioactivity after reaction equilibrium has been reached as set forth in Step B below; and
 (c) an antibody in sufficient quantity to bind a significant quantity of said selected radioactive h-βMSH peptide in the absence of any of the non-reactive big-h βMSH peptide to be measured;
B: allowing reaction of both the big h βMSH peptide, to be measured, and said selected radioactive h βMSH peptide, with said antibody to proceed substantially to equilibrium to thereby produce an antibody bound radioactive big-h βMSH peptide;
C: separating said antibody bound radioactive big-h βMSH peptide, to be measured, from said free radioactive big-h βMSH peptide;
D: measuring the quantity of radioactive big-h βMSH peptide selected from antibody bound radioactive big-h βMSH peptide and free radioactive big-βMSH peptide;
E: preparing a standard curve with known amounts of the big-h βMSH peptide to be measured; and
F: correlating the quantity of radioactive big-h βMSH peptide measured with a known amount of said big-βMSH peptide read from said standard curve.

20. The method of claim 16 which includes quantifying the level of α chain of the glycopeptide hormone by:
A: adding, to a measured quantity of human serum
 (a) buffering ions to buffer said serum;
 (b) radioactive α chain of the glycopeptide hormone, in an amount which will give a measurable counting rate of either antibody bound or free radioactivity after reaction equilibrium has been reached as set forth in Step B below; and
 (c) an antibody in sufficient quantity to bind a significant quantity of said radioactive α chain of the glycopeptide hormone in the absence of any of the non-radioactive α chain of the glycopeptide hormone to be measured;
B: allowing reaction of both the big h βMSH peptide, to be measured, and said selected radioactive h βMSH peptide, with said antibody to proceed substantially to equilibrium to thereby produce an antibody bound radioactive big-h βMSH peptide;
C: separating said antibody bound radioactive α chain of the glycopeptide hormone, to be measured, from said free radioactive chain of the glycopeptide hormone.
D: measuring the quantity of radioactive α chain of the glycopeptide hormone selected from antibody bound radioactive α chain of the glycopeptide hormone and free radioactive α chain of the glycopeptide hormone;
E: preparing a standard curve with known amounts of the α chain of the glycopeptide hormone; and
F: correlating the quantity of radioactive α chain of the glycopeptide hormone measured with a known amount of said α chain of the glycopeptide hormone read from said standard curve.

21. The method of claim 16 which includes quantifying the level of arginine vasoticin plus arginine vasopressin (AVT+AVP) by:

A: adding, to a measured quantity of human serum
 (a) buffering ions to buffer said serum;
 (b) radioactive AVP+AVT, in an amount which will give a measurable counting rate of either antibody bound or free radioactivity after reaction equilibrium has been reached as set forth in Step B below; and
 (c) an antibody in sufficient quantity to bind a significant quantity of said radioactive AVP+AVT in the absence of any of the non-radioactive AVP+AVT to be measured;
B: allowing reaction of both AVP+AVT, to be measured, and said radioactive AVP+AVT, with said antibody to proceed substantially to equilibrium to thereby produce an antibody bound radioactive AVP+AVT;
C: separating said antibody bound radioactive AVP+AVT, to be measured, from said free radioactive AVP+AVT;
D: measuring the quantity of radioactive AVP+AVT selected from antibody bound radioactive AVP+AVT and free radioactive AVP+AVT;
E: preparing a standard curve with known amounts of the AVP+AVT; and
F: correlating the quantity of radioactive AVP+AVT measured with a known amount of said AVP+AVT read from said standard curve.

22. The method of claim 21 which includes:
quantifying by radioimmunoassay the level of AVP, whereby AVT levels are measurable as the difference between the AVP+AVT value and AVP value.

23. A method of screening for cancer of certain tumor and histological types in humans, which includes the combination of the following steps:
 (i) measuring the level of big-ACTH (big-Adrenocorticotropin Hormone) peptide in human serum by radioimmunoassay of ACTH, assay of 1-39 amino acid ACTH and calculating the difference as big ACTH;
 (ii) measuring by radioimmunoassay, the level of big βMSH (big-melanocyte-stimulating hormone) peptide in human serum;
 (iii) measuring by radioimmunoassay, the level of the α chain of glycopeptide hormone in human serum;
 (iv) measuring by radioimmunoassay, the level of the peptide selected from the group consisting of argenine vasotocin (AVT) and argenine vasopressin (AVP plus argenine vasotocin (AVT) in human serum, the steps (i) through (iv) being performed in any sequence employing the kit of claim 1;
each radioimmunoassay including a measurement of the free or bound radioactive peptide; and
comparing the level of each of said peptides with normal values circulating in the blood of humans to determine the elevation, if any, of any of said peptides.

* * * * *